United States Patent

Chikusa et al.

Patent Number: 6,143,311
Date of Patent: Nov. 7, 2000

[54] IODOPROPARGYL DERIVATIVES AND ANTIMICROBIAL AGENTS COMPRISING THEM AS AN ACTIVE INGREDIENT

[75] Inventors: Yasuo Chikusa, Kobe; Keita Umetsu, Tatsuno; Shigeya Saijo, Nishinomiya; Masafumi Moriwaki, Kobe; Toshimasa Ohnishi, Tatsuno; Ikuya Tanaka, Tatsuno; Yuji Yanagida, Tatsuno, all of Japan

[73] Assignees: Nagase & Company, Ltd.; Nagase Chemicals Ltd., both of Osaka, Japan

[21] Appl. No.: 09/367,831

[22] PCT Filed: Feb. 25, 1998

[86] PCT No.: PCT/JP98/00750

§ 371 Date: Aug. 26, 1999

§ 102(e) Date: Aug. 26, 1999

[87] PCT Pub. No.: WO98/38148

PCT Pub. Date: Sep. 3, 1998

[30] Foreign Application Priority Data

Feb. 26, 1997 [JP] Japan ................................ 9-041878

[51] Int. Cl.[7] ................ A61K 31/275; A61K 31/075; C07C 255/59; C07C 43/12; A01N 25/34
[52] U.S. Cl. .................. 424/405; 514/720; 514/520; 558/423; 568/593
[58] Field of Search ............ 558/423; 514/520, 514/720; 568/593; 424/404, 405

[56] References Cited

U.S. PATENT DOCUMENTS

| | | | |
|---|---|---|---|
| 3,660,499 | 5/1972 | Kobayashi et al. | 260/613 |
| 3,923,870 | 12/1975 | Singer | 260/428 C |
| 4,487,781 | 12/1984 | Morisawa et al. | 424/301 |

FOREIGN PATENT DOCUMENTS

| | | | |
|---|---|---|---|
| 42-11734 | 7/1942 | Japan | 16/412 |
| 42-22364 | 11/1942 | Japan | 16/413 |
| 43-6609 | 3/1943 | Japan | 16/72 |

*Primary Examiner*—Joseph McKane
*Assistant Examiner*—Ebenezer Sackey
*Attorney, Agent, or Firm*—Jacobson, Price, Holman & Stern, PLLC

[57] ABSTRACT

The present invention provides novel iodopropargyl derivatives represented by the following formula (1):

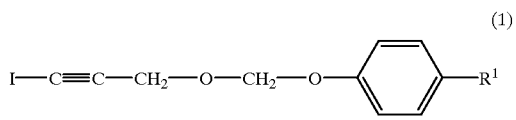

wherein $R^1$ is a methoxy group or a cyano group, which have a reduced unpleasant smell and also have a wide antimicrobial spectrum and a high antimicrobial activity. Also, the present invention provides antimicrobial, antifungal and preservative or antimold agents comprising the above derivatives as an active ingredient.

12 Claims, No Drawings

IODOPROPARGYL DERIVATIVES AND ANTIMICROBIAL AGENTS COMPRISING THEM AS AN ACTIVE INGREDIENT

This application is a 371 of PCT/JP98/00750 filed Feb. 25, 1998.

TECHNICAL FIELD

The present invention relates to novel iodopropargyl derivatives which have a reduced smell as well as a wide antimicrobial spectrum and a high antimicrobial activity. Moreover, it relates to antimicrobial, antifungal and also preservative or antimold agents comprising said derivatives as an active ingredient, which can be suitably used industrially.

BACKGROUND ART

It is hitherto known that an organic iodide series of antimicrobial agents such as 1-chloro-4-[[(3-iodo-2-propynyl)oxy]methoxy]benzene and 1-[[(3-iodo-2-propynyl)oxy]-methoxy]-3-methylbenzene, both of which are described in JP-B-47/24121 as 4-chlorophenyl 3-iodopropargyl formal and meta-cresyl 3-iodopropargyl formal, respectively, 3-bromo-2,3-diiodo-2-propenyl-ethylcarbonate and 3-iodo-2-propynyl-butylcarbamate are predominantly used for preservative and antimold purposes for wood. Moreover, antifungal agents such as phenyl-11-iodo-10-undecynoate and 3-iodo-2-propynyl-2,4,5-trichlorophenyl ether are known in the art. Although each of the above antimicrobial agents has a particular antimicrobial spectrum, it may have drawbacks such as a relatively high toxicity against the human body, an insufficient effect on particular microorganisms and/or a strong smell.

Among others, 1-chloro-4-[[(3-iodo-2-propynyl)oxy] methoxy]benzene has excellent properties such as a particularly high antimicrobial activity against mold and a low toxicity against the human body, and therefore, it is practically used based on these properties. However, the compound has a strong, characteristic, unpleasant smell. Thus, the compound gives rise to a difficulty in its application when used at a high concentration. Accordingly, the use of the compound is often limited to preservative and antimold purposes for wood stored outdoors.

Accordingly, the present inventors intended to develop compounds having a reduced smell together with a wide antimicrobial spectrum and a high antimicrobial activity.

DISCLOSURE OF THE INVENTION

In order to develop compounds having the above properties, the present inventors prepared a variety of iodopropargyl derivatives represented by the following formula (2):

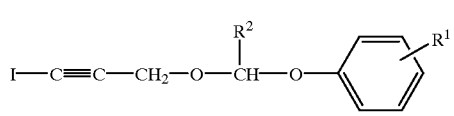

(2)

wherein $R^1$ is an alkoxy group or a cyano group, and $R^2$ is a hydrogen atom or a methyl group, and investigated their properties.

As a result, it was found that a particular iodopropargyl derivative has a reduced smell and also a wide antimicrobial spectrum and a high antimicrobial activity, and the present invention has been accomplished as follows.

The present invention provides iodopropargyl derivatives represented by the following formula (1):

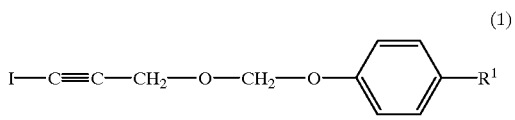

(1)

wherein $R^1$ is a methoxy group or a cyano group.

Also, the present invention provides antimicrobial, antifungal and preservative or antimold agents comprising the iodopropargyl derivatives of the above formula (1) as an active ingredient.

BEST MODE FOR PRACTICING THE INVENTION

In the following, the present invention is described in more detail.

In the context of the present invention, the term "antimicrobial agent" means an agent having an effect on inhibition of proliferation of microorganisms such as bacteria, fungi and algae or on killing of these microorganisms.

The term "antifungal agent" means an agent having an effect on inhibition of proliferation of fungi or on killing of fungi.

The term "preservative or antimold agent" means an agent having an effect on inhibition of proliferation of rot-inducing microorganisms or decay fungi or on killing of these microorganisms.

Among the iodopropargyl derivatives of the formula (2), there are a group of compounds which have a reduced smell as well as a wide antimicrobial spectrum and a high antimicrobial activity, as shown in the Examples below.

From the viewpoint of the antimicrobial activity, preferable compounds are those of the formula (2) wherein $R^1$ is a para-substituted methoxy or cyano group. More preferable compounds are those of the formula (2) wherein $R^1$ is a para-substituted methoxy or cyano group and $R^1$ is a hydrogen atom.

Furthermore, from the viewpoint of smell, preferable compounds are those of formula (2) wherein $R^1$ is an alkoxy or cyano group and $^2$ is a hydrogen atom and wherein $R^1$ is a para-substituted methoxy group and $^2$ is a methyl group. More preferable compounds are those of the formula (2) wherein $R^1$ is an alkoxy group and $R^2$ is a hydrogen atom and wherein $R^1$ is a para-substituted methoxy group and $^2$ is a methyl group.

Accordingly, compounds having a reduced smell together with a wide antimicrobial spectrum and a high antimicrobial activity are iodopropargyl derivatives of the formula (2) wherein $R^1$ is a para-substituted methoxy or cyano group and $R^2$ is a hydrogen atom, i.e. iodopropargyl derivatives of the above formula (1).

Among the compounds of the formula (1), the compound wherein $R^1$ is a methoxy group is particularly preferable.

Also, the present invention provides an antimicrobial agent comprising an iodopropargyl derivative of the formula (1) as an active ingredient, the one being preferably used for the antifungal or preservative or antimold agent.

The iodopropargyl derivatives of the formula (2) including the present iodopropargyl derivatives can be prepared, for example, according to the following reaction scheme I starting with propargyl alcohol:

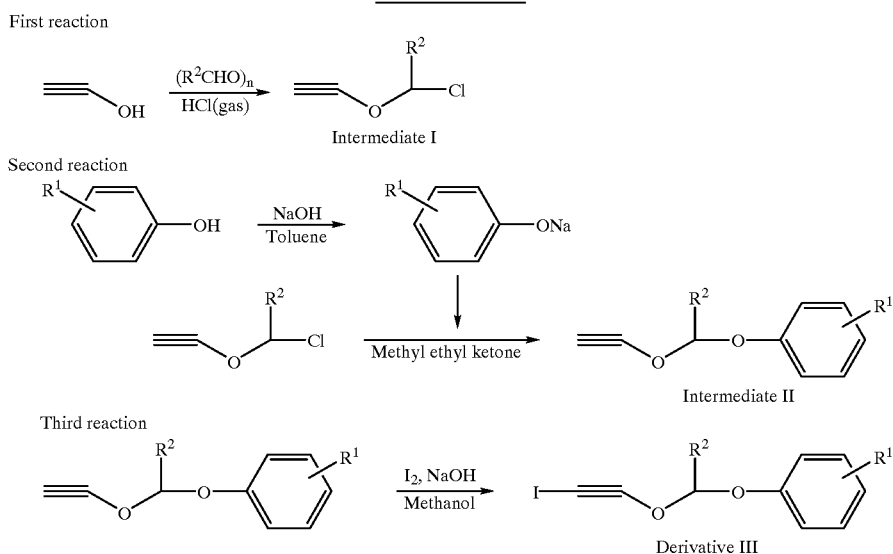

Reaction Scheme I wherein $R^1$ and $R^2$ are as specified for the above formula (2).

In the first reaction, propargyl alcohol (2-propyn-1-ol) is reacted with paraformaldehyde or paraldehyde in the presence of hydrogen chloride gas to obtain intermediate I. The reaction can be carried out in the absence of a solvent. The ratio of propargyl alcohol (2-propyn-1-ol) to paraformaldehyde or paraldehyde to be used in the reaction can be in the range of 1.0:1 to 1.2:1. The reaction temperature can be below 18° C. and the reaction usually completes within 3 to 5 hours.

In the second reaction, a substituted phenol such as p-methoxyphenol or p-cyanophenol is reacted with an alkali such as sodium hydroxide to obtain the corresponding alkali salt. The reaction can be carried out in a hydrocarbon such as toluene according to a conventional method.

The alkali salt of the substituted phenol thus prepared is reacted with intermediate I to obtain intermediate II. The reaction can be carried out in a ketone such as methyl ethyl ketone. The ratio of the alkali salt of the substituted phenol to intermediate I to be used in the reaction can be 1.0:1 to 1.2:1. The reaction temperature can be below about 40° C. and the reaction usually completes within about 3 hours.

In the third reaction, iodine is finally reacted with intermediate II to obtain the desired product, iodopropargyl derivative III. The reaction can be carried out in an alcohol such as methanol in the presence of an alkali such as sodium hydroxide. The ratio of iodine to intermediate II to be used in the reaction can be 0.8:1 to 1.0:1. The reaction temperature can be below 10° C. and the reaction usually completes within about 3 hours.

The present antimicrobial agent having a reduced smell as well as a wide antimicrobial spectrum and a high antimicrobial activity can be prepared by using the iodopropargyl derivatives obtained in the above reaction as an active ingredient.

The iodopropargyl derivatives according to the present invention can be used as an antimicrobial agent by themselves. Also, they can be used in any form of formulations by mixing them with emulsifiers, dispersants, carriers, stabilizers, excipients, organic foaming agents, etc. according to their usage.

The proportion of an iodopropargyl derivative in the antimicrobial agent disclosed herein may be adequately chosen depending on objects to be applied, formulations to be prepared and methods to be used. In general, an iodopropargyl derivative is usually used in an amount of 0.1 to 99% by weight and preferably in an amount of 0.5 to 50% by weight, based on an antimicrobial agent as a whole.

Since the antimicrobial agents according to the present invention are superior, in particular, in preservative and antimold properties, they are suitably applied to various industrial products (for example, paints, emulsions, inks, sizes, metal working fluids, plastics, fibers, wood, leather, resin moldings, etc.) or materials therefor. The antimicrobial agents according to the present invention can be used by direct coating or spraying. Alternatively, the objects may be immersed in the antimicrobial agents according to the present invention.

EXAMPLES

The present invention is illustrated in more detail based on the following examples and comparative examples, but it is not limited thereto.

In these examples and comparative examples, melting points were measured by using a differential calorimeter DSC7 (Parkin Elmer LLC). Nuclear magnetic resonance spectra (hereinafter abbreviated as $^1$H-NMR) were recorded by using a UNITY-400 apparatus (Varian Inc.) and infrared spectra (hereinafter abbreviated as IR) by using 1600 Series FTIR (Parkin Elmer LLC).

Chemical purity was assessed by gas chromatography GC-14A (Shimadzu Corporation) or high performance liquid chromatography LC Model I (Waters Co.).

EXAMPLE 1

Preparation of Chloromethyl 2-Propynyl Ether (Intermediate I-a)

Hydrogen chloride gas was blown into a mixture of 2-propyn-1-ol (137.2 g, 2.4 mol) and paraformaldehyde (63.2 g, 2.0 mol) at a temperature below 15° C. After completion of the reaction was confirmed by gas chromatography, water formed during the reaction was separated from the reaction solution to give a crude reaction product (199 g). Its chemical purity by gas chromatography (hereinafter abbreviated as GC) was 91%.

The crude product was purified by distillation (55 to 58° C., 100 mmHg) to obtain the desired chloromethyl 2-propynyl ether (168 g, 80.0% yield). Chemical purity by GC was 99.5%.

| Conditions of GC analysis: | |
|---|---|
| Column | G-100, 40 m × 1.2 mm (Kagakuhin Kensa Kyokai); |
| Injection temp. | 250° C.; |
| Detection temp. | 280° C.; |
| Column temp. | |
| initial | 45° C./5 min.; |
| elevation | 15° C./min.; |
| top | 230° C. |
| Detection | FID. |

EXAMPLE 2
Preparation of 1-Methoxy-4-[(2-propynyloxy)methoxy]benzene (Intermediate II-a)

A sodium salt of p-methoxyphenol(14.6 g, 0.1 mol) was dissolved in methyl ethyl ketone (30 ml), and chloromethyl 2-propynyl ether (Intermediate I-a)(10.6 g, 0.1 mol) prepared in example 1 was added dropwise to the solution with stirring at room temperature. The reaction mixture was stirred for further 2 hours and the solvent was then evaporated off. The residue was washed with distilled water (20 g) and extraction with toluene (30 ml) was carried out to obtain a crude reaction product (19 g). Its chemical purity by high performance liquid chromatography (hereinafter abbreviated as HPLC) was 80%.

The crude product was purified by distillation (118 to 120° C., 5 mmHg) to obtain 1-methoxy-4-[(2-propynyloxy)methoxy]benzene (Intermediate II-a) (13.0 g, 66.4% yield). Its chemical purity by HPLC was 99.5%.

| Conditions of HPLC analysis: | |
|---|---|
| Column | CAPCELL PAK C-18 (Shiseido Co., Ltd.); |
| Mobile phase | methanol:water:acetic acid = 65:35:0.3; |
| Flow rate | 2 ml/min.; |
| Column temp. | 25° C.; |
| Detection | 224 nm. |

EXAMPLE 3
Preparation of 1-[[(3-Iodo-2-propynyl)oxy]methoxy]-4-methoxybenzene (Derivative III-a)

1-Methoxy-4-[(2-propynyloxy)methoxy]benzene (Intermediate II-a) (9.8 g, 0.5 mol) prepared in the above example 2 and 48% w/v aqueous sodium hydroxide solution (11.0 g) were added to methanol (75 g). Iodine (14.0 g, 0.055 mol) was then added to the solution in several portions during which the inner temperature was maintained at below 10° C. The reaction mixture was stirred for further 3 hours and the solvent was then evaporated off. The residue was extracted with toluene (20 ml) and the toluene layer was washed with distilled water. Toluene was then evaporated off to obtain the desired 1-[[(3-iodo-2-propynyl) oxy]methoxy]-4-methoxybenzene (Derivative III-a)(12.6 g).

Analytical results of this compound are shown below:
Melting point (DSC):31.6° C.;
IR (KBr) [ν(cm$^{-1}$)]:2958, 2905, 2836, 2189, 1511, 1210;
$^1$H-NMR (CDCl$_3$)[δ(ppm)]:6.97 (d, J=9.0 Hz, 2H), 6.82 (d, J=9.0 Hz, 2H), 5.24 (s, 2H), 4.48 (s, 2H), 3.76 (s, 3H);

Chemical purity (HPLC analysis under the same conditions as described in example 2):99.8%.

For comparison purposes, various iodopropargyl derivatives were prepared from their corresponding starting compounds according to the similar methods to those described in examples 1 to 3. Analytical results of these derivatives are shown below:

Comparative Example 1
1-Ethoxy-4-[[(3-iodo-2-propynyl)oxy]methoxy]benzene (Derivative III-b)

Melting point (DSC analysis):66.1° C.;
$^1$H-NMR [δ(ppm)]:6.96 (d, J=9.2 Hz, 2H), 6.81 (d, J=9.2 Hz, 2H), 5.23 (s, 2H), 4.46 (s, 2H), 3.98 (dd, J=6.8, 14 Hz, 2H), 1.39 (t, J=6.8 Hz, 3H).

Comparative Example 2
1-[[(3-Iodo-2-propynyl)oxy]methoxy]-2-methoxybenzene (Derivative III-c)

Melting point: 69.1° C.;
$^1$H-NMR [δ(ppm)]:7.15–6.87 (m, 4H), 5.34 (s, 2H), 4.53 (s, 2H), 3.87 (s, 3H).

Comparative Example 3
1-Ethoxy-2-[[(3-iodo-2-propynyl)oxy]methoxy]benzene (Derivative III-d)

Melting point: 44.0° C.;
$^1$H-NMR [δ(ppm)]:7.13–6.86 (m, 4H), 5.33 (s, 2H), 4.56 (s, 2H), 4.09 (dd, J=7.2, 14 Hz, 2H), 1.45 (t, J=7.2 Hz, 3H)

Comparative Example 4
1-[1-[(3-Iodo-2-propynyl)oxy]ethoxy]-4-methoxybenzene (Derivative III-e)

Boiling point: 135° C./0.12 mmHg;
$^1$H-NMR [δ(ppm)]:6.96–6.81 (m, 4H), 5.39 (dd, J=5.2, 10.4 Hz, 1H), 4.47 (dd, J=16, 22 Hz, 2H), 3.77 (s, 3H), 1.47 (d, J=5.6 Hz, 3H).

Comparative Example 5
1-Ethoxy-4-[1-[(3-Iodo-2-propynyl)oxy]ethoxy]benzene (Derivative III-f)

Boiling point: 135° C./0.12 mmHg;
$^1$H-NMR [δ(ppm)]:6.95–6.80 (m, 4H), 5.38 (dd, J=5.2, 10.4 Hz, 1H), 4.47 (dd, J=16, 22 Hz, 2H), 3.99 (dd, J=6.8, 14 Hz, 2H), 1.47–1.38 (m, 6H).

Comparative Example 6
1-[1-[(3-Iodo-2-propynyl)oxy]ethoxy]-2-methoxybenzene (Derivative III-g)

Boiling point: 132° C./0.12 mmHg;
$^1$H-NMR [δ(ppm)]:7.07–6.86 (m, 4H), 5.46 (dd, J=5.2, 10.8 Hz, 1H), 4.55 (s, 2H), 3.85 (s, 3H), 1.51 (d, J=5.2 Hz, 3H).

Comparative Example 7
1-Ethoxy-2-[1-[(3-iodo-2-propynyl)oxy]ethoxy]benzene (Derivative III-h)

Boiling point: 135° C./0.12 mmHg;
$^1$H-NMR [δ(ppm)]:7.06–6.85 (m, 4H), 5.41 (dd, J=5.2, 10.4 Hz, 1H), 4.58 (s, 2H), 4.07 (dd, J=6.8, 14 Hz, 2H), 1.50–1.43 (m, 6H).

EXAMPLE 4
Preparation of 1-Cyano-4-[(2-propynyloxy)methoxy]benzene (Intermediate II-i)

A sodium salt of p-cyanophenol(14.1 g) was dissolved in methyl ethyl ketone (20 ml), and chloromethyl 2-propynyl ether (Intermediate I-a) (10.6g, 0.1 mol) prepared in example 1 was added dropwise to the solution with stirring at room temperature. The reaction mixture was stirred for further 2 hours and the solvent was then evaporated off. The residue was extracted with toluene (30 ml) and the organic layer was washed with distilled water (20 g). The solvent was then evaporated off to obtain a crude reaction product (18.7 g). This was recrystallized from hexane (60 ml) to obtain 1-cyano-4-[(2-propynyloxy)methoxy]benzene (Intermediate II-i) (15.0 g, 79.7% yield). Its chemical purity by HPLC was 99.0%.

| Conditions of HPLC analysis: | |
|---|---|
| Column | CAPCELL PAK C-18 (Shiseido Co., Ltd.); |
| Mobile phase | methanol:water:acetic acid = 65:35:0.3; |
| Flow rate | 2 ml/min.; |
| Column temp. | 25° C.; |
| Detection | 224 nm. |

EXAMPLE 5
Preparation of 1-Cyano-4-[[(3-iodo-2-propynyl)oxy]methoxy]benzene (Derivative III-i)

1-Cyano-4-[(2-propynyloxy)methoxy]benzene (Intermediate II-i) (9.4 g, 0.05 mol) prepared in the above example 4 and 48% w/v aqueous sodium hydroxide solution (11.3 g) were added to methanol (75 g). Iodine (14.0 g, 0.055 mol) was then added to the solution in several portions while maintaining the inner temperature below 10° C. The reaction mixture was stirred for further 3 hours and the solvent was then evaporated off. The residue was extracted with toluene (10 ml) and the toluene layer was washed with distilled water. Toluene was then evaporated off to obtain a crude reaction product (15.3 g). The crude reaction product (15.3 g) was recrystallized from hexane (50 ml) to obtain the desired 1-cyano-4-[[(3-iodo-2-propynyl)oxy]methoxy]benzene (Derivative III-i)(12.6 g, 94% yield).

Analytical results of this compound are shown below:
Melting point (DSC): 100° C.;
IR (KBr) [ν(cm$^{-1}$)]:2227, 2185, 1604, 1507;
$^1$H-NMR (CDCl$_3$) [δ(ppm)]:4.6 (s, 2H), 5.4 (s, 2H), 7.1–7.6 (m, 4H);

Chemical purity (HPLC analysis under the same conditions as described in example 4):96.8%.

EXAMPLE 6
Evaluation of Antimicrobial Activity of Various Iodopropargyl Derivatives The minimum inhibitory concentration (hereinafter abbreviated as MIC) against four bacteria (*Enterobacter aerogenes, Eschericia coli, Pseudomonas aeruginosa* and *Bacillus subtillis*) and four fungi (*Aspergillus niger, Penicillium funiculosum, Gliocladium virens* and *Trichoderma viride*) was measured and used as an indicator of the antimicrobial activity.

The MIC against bacteria was measured as follows. The test bacteria were cultivated by inoculating a nutrient broth with them and keeping the mixture at 37° C. for 6 hours. On the other hand, the test media were prepared by adding solutions (0.2 ml) of an iodopropargyl derivative in dimethylformamide (DMF) at varying concentrations to the nutrient broth (10 ml). The above bacterial culture (0.1 ml) was added to the test media and the mixtures were cultivated at 30° C. for 24 hours. Then, the presence or absence of microorganism growth was assessed by observing the turbidity of media, by which the MIC was determined.

The MIC against fungi was measured as follows. The test fungal spores were suspended in sterilized water supplemented with a wetting agent. On the other hand, test media were prepared by adding solutions (0.3 ml) of an iodopropargyl derivative in dimethylformamide (DMF) at varying concentrations to a potato-dextrose-agar (PDA) medium (15 ml). The above spore suspensions (1 ml) were spread over the test media and the media were cultivated at 28° C. for 2 weeks. The presence or absence of fungal growth on the media was then observed to determine the MIC.

The results of these tests are shown in Table 1 below. The MIC of 1-chloro-4-[[(3-Iodo-2-propynyl)oxy]methoxy]benzene is also shown in Table 1 as a control.

TABLE 1

(2)

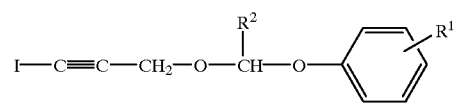

| Test compound [Formula (2)] | | | | Antimicrobial activity (MIC, ppm) | | | |
|---|---|---|---|---|---|---|---|
| Derivative | | | | Bacteria | | | |
| No. | Reference | R$^1$ | R$^2$ | A | B | C | D |
| — | — | p-chloro | hydrogen | >1000 | 100–200 | >1000 | 10–20 |
| III-a | Example 3 | p-methoxy | hydrogen | >1000 | >1000 | >1000 | 10–20 |
| III-b | Comp. Ex. 1 | p-ethoxy | hydrogen | >1000 | >1000 | >1000 | 100–200 |
| III-c | Comp. Ex. 2 | o-methoxy | hydrogen | >1000 | >1000 | >1000 | 200–400 |
| III-d | Comp. Ex. 3 | o-ethoxy | hydrogen | >1000 | >1000 | >1000 | 20–40 |
| III-e | Comp. Ex. 4 | p-methoxy | methyl | >1000 | >1000 | >1000 | 20–40 |
| III-f | Comp. Ex. 5 | p-ethoxy | methyl | >1000 | 400–1000 | >1000 | 10–20 |
| III-g | Comp. Ex. 6 | o-methoxy | methyl | >1000 | >1000 | >1000 | 20–40 |
| III-h | Comp. Ex. 7 | o-ethoxy | methyl | >1000 | >1000 | >1000 | 20–40 |
| III-i | Example 5 | p-cyano | hydrogen | >1000 | >1000 | >1000 | 20–40 |

TABLE 1-continued $$I-C\equiv C-CH_2-O-\underset{\underset{R^2}{|}}{CH}-O-\text{C}_6H_4-R^1 \quad (2)$$

| Test compound [Formula (2)] | | | | Antimicrobial activity (MIC, ppm) | | | |
|---|---|---|---|---|---|---|---|
| Derivative | | | | Fungi | | | |
| No. | Reference | $R^1$ | $R^2$ | E | F | G | H |
| — | — | p-chloro | hydrogen | 0.4–1 | 0.4–1 | 1–2 | 1–2 |
| III-a | Example 3 | p-methoxy | hydrogen | 0.4–1 | 2–4 | 2–4 | 0.4–1 |
| III-b | Comp. Ex. 1 | p-ethoxy | hydrogen | 4–10 | >20 | >20 | 4–10 |
| III-c | Comp. Ex. 2 | o-methoxy | hydrogen | 10–20 | >20 | >20 | 10–20 |
| III-d | Comp. Ex. 3 | o-ethoxy | hydrogen | 1–2 | 4–10 | 4–10 | 1–2 |
| III-e | Comp. Ex. 4 | p-methoxy | methyl | 0.4–1 | 2–4 | 4–10 | 1–2 |
| III-f | Comp. Ex. 5 | p-ethoxy | methyl | 1–2 | 4–10 | 4–10 | 1–2 |
| III-g | Comp. Ex. 6 | o-methoxy | methyl | 1–2 | 2–4 | 4–10 | 2–4 |
| III-h | Comp. Ex. 7 | o-ethoxy | methyl | 2–4 | 2–4 | 4–10 | 2–4 |
| III-i | Example 5 | p-cyano | hydrogen | 1–2 | 0.4–1 | 0.4–1 | 0.4–1 |

A: *Enterobacter aerogenes*
B: *Eschericia coli*
C: *Pseudomonas aeruginosa*
D: *Bacillus subtillis*
E: *Aspergillus niger*
F: *Penicillium funiculosum*
G: *Gliocladium virens*
H: *Trichoderma viride*

From these results, it can be seen that 1-[[(3-iodo-2-propynyl)oxy]methoxy]-4-methoxybenzene (Derivative III-a), 1-[1-[(3-iodo-2-propynyl)oxy]ethoxy]-4-methoxybenzene (Derivative III-e) and 1-cyano-4-[[((3-iodo-2-propynyl)oxy]methoxy]benzene (Derivative III-i) are superior to the others in the antimicrobial activity. In particular, it can be seen that 1-[[(3-iodo-2-propynyl)oxy]methoxy]-4-methoxybenzene (Derivative III-a) and 1-cyano-4-[[(3-iodo-2-propynyl)oxy]methoxy]benzene (Derivative III-i) show an antimicrobial activity similar to that of 1-chloro-4-[[(3-iodo-2-propynyl)oxy]methoxy]benzene used as a control.

EXAMPLE 7

Sensing Test of Smell

A sensing test of smell was carried out for the various iodopropargyl derivatives. Samples (1.0 g) were added into sample tubes and the magnitude of smell and the degree of pleasant/unpleasant smell were assessed by thirteen examiners. The assessment was carried out by using "six ranks of smell magnitude indication" and "seven ranks of pleasant/unpleasant smell indication" as shown below in Table 2. The results were expressed numerically and the average values of the scores from the thirteen examiners are shown. 1-Chloro-4-[[(3-iodo-2-propynyl)oxy]methoxy]benzene (technical grade; abbreviated as IF-1000) was used as a control and its score was set as "5" for "six ranks of smell magnitude indication" and "–3" for "seven ranks of pleasant/unpleasant smell indication".

TABLE 2

| Six ranks of smell magnitude indication | Seven ranks of pleasant/unpleasant smell indication |
|---|---|
| 0 not sensed | +3 pleasant |
| 1 slightly sensed | +2 fairly pleasant |
| 2 fairly sensed | +1 slightly pleasant |
| 3 strongly sensed | 0 not pleasant nor unpleasant |
| 4 very strongly sensed | –1 slightly unpleasant |
| 5 extremely strongly sensed | –2 fairly unpleasant |
| | –3 unpleasant |

The results of these tests are shown in Table 3 below.

TABLE 3

| Sample name | Smell magnitude indication | Pleasant/unpleasant smell indication |
|---|---|---|
| IF-1000 | 5 | –3 |
| Derivative III-a | 1.5 | –0.5 |
| Derivative III-b | 1.1 | –0.1 |
| Derivative III-c | 1.0 | +0.2 |
| Derivative III-d | 1.1 | –0.2 |
| Derivative III-e | 1.2 | –0.3 |
| Derivative III-f | 2.8 | –0.6 |
| Derivative III-g | 2.9 | –0.2 |
| Derivative III-h | 2.9 | –1.2 |
| Derivative III-i | 2.0 | –0.8 |

From these results, it is apparent that all the derivatives are superior to the control substance in both the smell magnitude and pleasant/unpleasant smell indications. In particular, the smell magnitude has been greatly reduced with the derivatives III-a, III-b, III-c, III-d, III-e and III-i.

EXAMPLE 8

Preparation of Various Antimicrobial Agents And Their Applications For Preservative or Antimold Purposes Various antimicrobial agents were prepared by using the iodopropargyl derivatives according to the present invention and applied as illustrated below.

(1) Antimold Agent for Wood (a) Preparation

The following ingredients were mixed and stirred to prepare an antimold agent for wood.

TABLE 4

| Ingredients | Amount (parts by weight) |
| --- | --- |
| 1. Derivative III-a | 10 |
| 2. Polyoxyethylene styryl phenyl ether | 15 |
| 3. Diethylene glycol monomethyl ether | 75 |

(b) Application

The agent prepared above was diluted with water with stirring until a given concentration (dilution rate) was achieved. An immersing treatment of wood was carried out by immersing a sapwood (a flat-grain woodboard having a rough surface and having dimensions of 1 cm thick, 10 cm width and 40 cm length) of Japanese red pine, immediately after sawing it, in the above diluted solution for 3 minutes.

(c) Assessment

The antimold activity for wood was assessed by the following method. Five woodboards treated under the same conditions were bound, and each bundle was covered with a vinyl tarpaulin and left wet for three months. The assessment was carried out by visually observing a growth state of mold on the surface of each test woodboard, according to the ratings listed below.

TABLE 5

| Rating | Growth state of mold |
| --- | --- |
| 0 | No mold growth observed on board surface |
| 1 | Mold growth observed within about 10% on board surface |
| 2 | Mold growth observed in about 10 to 25% on board surface |
| 3 | Mold growth observed in about 25 to 50% on board surface |
| 4 | Mold growth observed in at least about 50% on board surface |

(d) Results

The results obtained by averaging the ratings for the woodboards treated under the same treatment condition are summarized below in Table 6.

TABLE 6

| Dilution rate | Average rating |
| --- | --- |
| Untreated | 4.0 |
| 100-fold | 0 |
| 200-fold | 0.3 |
| 300-fold | 0.8 |

(2) Preservative Agent for Wood (a) Preparation

The following ingredients were mixed and stirred to prepare a preservative agent for wood.

TABLE 7

| Ingredients | Amount (parts by weight) |
| --- | --- |
| 1. Derivative III-i | 0.6 |
| 2. Naphthenic solvent | 99.4 |

(b) Application

The cut ends of a wood piece (5 mm thick, 20 mm wide and 40 mm long with the 40×20 mm plane being a straight-grain one) of cedar or beech were covered with an epoxy resin. The agent prepared above was diluted half at the effective concentration and applied to the wood piece (110 g/m$^2$). After air-drying for 20 days, each wood piece was immersed in static water (volume ratio of water to the wood piece=10:1) at 25° C. for 5 hours and water was evaporated at 40° C. over 19 hours. Such weathering procedures were repeated 30 times. The same weathering procedures were also applied to an untreated wood piece. After completing the weathering procedures, wood pieces were dried at 60° C. for 48 hours and weighed (W1).

(c) Assessment

The preservative activity for wood was assessed by the following method. The wood pieces treated as above were put into an incubator in which a decay fungus (Tyromyces palustris or Coriolus versicolor) had been cultivated, and stored there for 8 weeks at a temperature of 26° C. under a humidity of 70%. The wood pieces thus challenged were taken out of the incubator, and hyphae and other materials attached to them were removed. The wood pieces were air-dried at 25° C. for 24 hours, dried with heating at 60° C. for 48 hours, and then weighed (W2). The erosion rate (rate of weight loss) caused by a decay fungus was calculated by the following formula. In this experiment, cedar wood was used for Tyromyces palustris and beech wood was used for Coriolus versicolor.

$$\text{Rate of weight loss } (\%) = (W1-W2)/W1 \times 100$$

wherein W1 is the weight of the wood piece before decay induction, and W2 is the weight of the wood piece after decay induction.

(d) Results

The results of these tests are summarized below in Table 8.

TABLE 8

| Microorganism | Wood | Treatment of wood | Weight loss (%) | Decay resistance |
| --- | --- | --- | --- | --- |
| Tyromyces palustris | Cedar | + | 0 | + |
|  |  | − | 34.7 | − |
| Coriolus versicolor | Beech | + | 0 | + |
|  |  | − | 28.5 | − |

(3) Antifungal Agent for Coating (a) Preparation

The following ingredients were mixed and stirred to prepare an antifungal agent for coating.

TABLE 9

| Ingredients | Amount (parts by weight) |
| --- | --- |
| 1. Derivative III-a | 10 |
| 2. Dibutyl phthalate | 90 |

(b) Application

The agent prepared above was added to an acrylic emulsion paint at a given concentration. The paint was uniformly coated onto a No. 5 qualitative filter paper in the amount equal to the weight of the filter paper. The filter paper thus applied was dried and used as a test piece. The test piece was subjected to weathering procedures as follows. The piece was immersed in water (200 ml) at room temperature for 18 hours, air-dried at room temperature for 2 hours and dried with heating at 80° C. for 2 hours.

(c) Assessment

The test piece was put on an agar plate (1000 ml distilled water, 40 g glucose, 10 g peptone and 25 g agar). A spore suspension (1 ml) of five fungi (*Aspergillus niger, Penicillium funiculosum, Cladosporium cladosporioides, Aureobasidium pullulans* and *Gliocladium virens*), which had been grown on slants in a test tube, was sprayed onto the surface of both the agar plate and the test piece. They were then incubated at a temperature of 28° C. for 7 days and the growth state of the microorganisms on the test piece was observed.

The results were assessed according to the ratings listed below.

TABLE 10

| Rating | Growth state of fungi |
| --- | --- |
| 1 | No growth of fungi observed on test piece |
| 2 | Growth of fungi observed within 1/10 on surface of test piece |
| 3 | Growth of fungi observed in 1/10 to 1/3 on surface of test piece |
| 4 | Growth of fungi observed in at least 1/3 on surface of test piece |

(d) Results

The results of these tests are summarized below in Table 11.

TABLE 11

| Amount of derivative III-a added (ppm) | Rating |
| --- | --- |
| 0 | 4 |
| 250 | 2 |
| 500 | 1 |
| 1000 | 1 |
| 2000 | 1 |

INDUSTRIAL UTILIZATION

The iodopropargyl derivatives according to the present invention have a wide antimicrobial spectrum and an excellent antimicrobial activity and also have a reduced smell. Accordingly, not only these iodopropargyl derivatives but also antimicrobial, antifungal and preservative or antimold agents comprising said derivatives as an active ingredient can be applied to various industrial products or materials therefor.

What is claimed is:

1. An iodopropargyl derivative represented by the following formula (1):

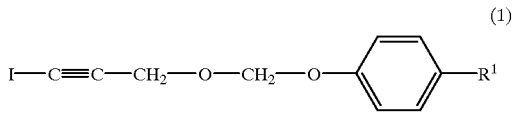

wherein $R^1$ is a methoxy group or a cyano group.

2. The iodopropargyl derivative according to claim 1 wherein $R^1$ is a methoxy group.

3. The iodopropargyl derivative according to claim 1 wherein $R^1$ is a cyano group.

4. An antimicrobial agent comprising an iodopropargyl derivative according to claim 1 and a suitable carrier therefor.

5. An antimicrobial agent comprising the iodopropargyl derivative according to claim 2 and a suitable carrier therefor.

6. An antimicrobial agent comprising the iodopropargyl derivative according to claim 3 and a suitable carrier therefor.

7. An antifungal agent comprising an iodopropargyl derivative according to claim 1 and a suitable carrier therefor.

8. An antifungal agent comprising the iodopropargyl derivative according to claim 2 and a suitable carrier therefor.

9. An antifungal agent comprising the iodopropargyl derivative according to claim 3 and a suitable carrier therefor.

10. A preservative or antimold agent comprising an iodopropargyl derivative according to claim 1 and a suitable carrier therefor.

11. A preservative or antimold agent comprising the iodopropargyl derivative according to claim 2 and a suitable carrier therefor.

12. A preservative or antimold agent comprising the iodopropargyl derivative according to claim 3 and a suitable carrier therefor.

* * * * *